United States Patent [19]

Cherpeck

[11] Patent Number: 5,786,499
[45] Date of Patent: Jul. 28, 1998

[54] AROMATIC AMIDES OF POLY (OXYALKYLENE)CARBAMATES AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 667,899

[22] Filed: Jun. 20, 1996

[51] Int. Cl.$^6$ .................................. C07C 271/12
[52] U.S. Cl. .................. 560/27; 560/21; 560/22; 560/23; 560/24; 560/29
[58] Field of Search .................. 44/387, 334, 335, 44/338, 340; 560/21, 22, 23, 24, 27, 29

[56] References Cited

U.S. PATENT DOCUMENTS

| | | | |
|---|---|---|---|
| 2,714,607 | 8/1955 | Matter | 260/471 |
| 3,652,240 | 3/1972 | Dorn et al. | 44/66 |
| 3,849,085 | 11/1974 | Kreuz et al. | 44/78 |
| 4,134,846 | 1/1979 | Machleder et al. | 252/51.5 A |
| 4,191,537 | 3/1980 | Lewis et al. | 44/71 |
| 4,320,021 | 3/1982 | Lange | 252/51.5 R |
| 4,328,322 | 5/1982 | Baron | 521/163 |
| 4,347,148 | 8/1982 | Davis | 252/51.5 R |
| 4,600,409 | 7/1986 | Campbell | 44/75 |
| 4,859,210 | 8/1989 | Franz et al. | 44/53 |
| 4,952,732 | 8/1990 | Speranza et al. | 564/390 |
| 5,090,914 | 2/1992 | Reardan et al. | 435/188 |
| 5,413,614 | 5/1995 | Cherpeck | 44/387 |
| 5,484,463 | 1/1996 | Cherpeck | 44/387 |

*Primary Examiner*—Shailendra Kumar
*Attorney, Agent, or Firm*—Claude J. Caroli

[57] ABSTRACT

Aromatic amides of poly(oxyalkylene) carbamates having the formula:

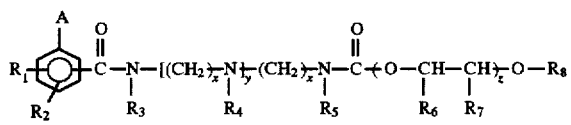

or a fuel-soluble salt thereof; wherein A, $R_1$–$R_{10}$, x, y, and z are as defined herein.

20 Claims, No Drawings

AROMATIC AMIDES OF POLY (OXYALKYLENE)CARBAMATES AND FUEL COMPOSITIONS CONTAINING THE SAME

CROSS-REFERENCE TO RELATED APPLICATIONS

This application claims priority from U.S. Provisional application Ser. No. 60/000,969, filed Jul. 6, 1995.

BACKGROUND OF THE INVENTION

1. Field of the Invention

This invention relates to novel hydroxy, nitro, and amino aromatic compounds. More particularly, this invention relates to novel hydroxy, nitro, and amino aromatic amides of poly(oxyalkylene)carbamates and their use in fuel compositions to prevent and control engine deposits.

2. Description of the Related Art

It is well known that automobile engines tend to form deposits on the surface of engine components, such as carburetor ports, throttle bodies, fuel injectors, intake ports, and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to about 0.25 volume percent of a high molecular weight aliphatic hydrocarbon-substituted phenol in which the aliphatic hydrocarbon radical has an average molecular weight in the range of about 500 to about 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants, and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Nitro phenols have also been employed as fuel additives. For example, U.S. Pat. No. 4,347,148, issued Aug. 31, 1982 to K. E. Davis, discloses nitro phenols containing at least one aliphatic substituent having at least about 40 carbon atoms. The nitro phenols of this patent are taught to be useful as detergents, dispersants, antioxidants, and demulsifiers for lubricating oil and fuel compositions.

Fuel additives containing a poly(oxyalkylene) moiety are also known in the art. For example, U.S. Pat. No. 2,714,607, issued Aug. 2, 1955 to M. Matter, discloses polyethoxy esters of aminobenzoic acids, nitrobenzoic acids, and other isocyclic acids. These polyethoxy esters are taught to have excellent pharmacological properties and to be useful as anesthetics, spasmolytics, analeptics, and bacteriostatics.

More recently, U.S. Pat. No. 4,191,537, issued Mar. 4, 1980 to R. A. Lewis et al., discloses a fuel composition comprising a major portion of hydrocarbons boiling in the gasoline range and from about 30 to about 2,000 ppm of a hydrocarbyl poly(oxyalkylene) aminocarbamate having a molecular weight from about 600 to about 10,000 and at least one basic nitrogen atom. The hydrocarbyl poly (oxyalkylene) moiety is composed of oxyalkylene units selected from about 2 to about 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde, and an alkylamine containing propoxy groups and, optionally, ethoxy groups. These Mannich condensates are taught to be useful as corrosion inhibitors, water repellent agents, paint adhesion promoters, and also as intermediates for preparing surfactants, and polyols finding use in the manufacture of polyurethane foam.

Similarly, U.S. Pat. No. 5,090,914, issued Feb. 25, 1992 to D. T. Reardan et al., discloses poly(oxyalkylene) aromatic compounds having an amino or hydrazinocarbonyl substituent on the aromatic moiety and an ester, amide, carbamate, urea, or ether linking group between the aromatic moiety and the poly(oxyalkylene) moiety. These compounds are taught to be useful for modifying macromolecular species such as proteins and enzymes.

U.S. Pat. No. 4,328,322, issued Sep. 22, 1980 to R. C. Baron, discloses amino- and nitrobenzoate esters of oligomeric polyols, such as poly(ethylene) glycol. These materials are used in the production of synthetic polymers by reaction with a polyisocyanate.

U.S. Pat. No. 4,859,210, issued Aug. 22, 1989 to Franz et al., discloses fuel compositions containing (1) one or more polybutyl or polyisobutyl alcohols wherein the polybutyl or polyisobutyl group has a number average molecular weight of about 324 to about 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic, mono- or polycarboxylic acids.

It has now been discovered that certain hydroxy, nitro, and amino aromatic amides of poly(oxyalkylene)carbamates provide excellent control of engine deposits, especially intake valve deposits, when employed as fuel additives in fuel compositions.

SUMMARY OF THE INVENTION

The present invention provides novel hydroxy, nitro, and amino aromatic amides of poly(oxyalkylene)carbamates which are useful as fuel additives for the prevention and control of engine deposits, particularly intake valve deposits.

The novel hydroxy, nitro, and amino aromatic amides of poly(oxyalkylene)cardamates of the present invention have the formula:

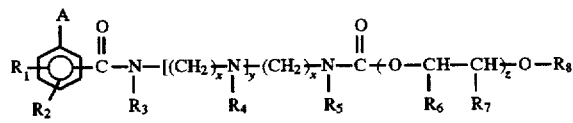

amount of a hydroxy, nitro, or amino aromatic amide of poly(oxyalkylene)carbamates of the present invention.

The present invention additionally provides a fuel concentrate comprising an inert stable oxophilic organic solvent boiling in the range of from about 150° F. to about 400° F. (about 65° C. to about 205° C.) and from about 10 to about 70 weight percent of a hydroxy, nitro, or amino aromatic amide of poly(oxyalkylene)carbamates of the present invention.

Among other factors, the present invention is based on the surprising discovery that certain hydroxy, nitro, and amino aromatic amides of poly(oxyalkylene)carbamates, when employed as fuel additives in fuel compositions, provide excellent control of engine deposits, especially on intake valves.

DETAILED DESCRIPTION OF THE INVENTION

The fuel additives provided by the present invention have the general formula:

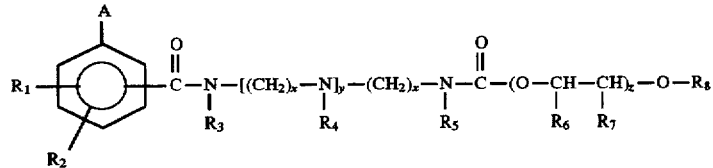

or a fuel-soluble salt thereof; wherein A is hydroxy, nitro, amino, N-alkylamino wherein the alkyl group contains about 1 to about 6 carbon atoms, or N,N-dialkylamino wherein each alkyl group independently contains about 1 to about 6 carbon atoms; $R_1$ and $R_2$ are each independently hydrogen, hydroxy, lower alkyl having about 1 to about 6 carbon atoms, or lower alkoxy having about 1 to about 6 carbon atoms; $R_3$ and $R_3$ are each independently hydrogen or lower alkyl having about 1 to about 6 carbon atoms; $R_4$ is hydrogen or an acyl group of the formula:

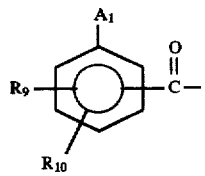

wherein $A_1$ is hydroxy, nitro, amino, N-alkylamino wherein the alkyl group contains about 1 to about 6 carbon atoms, or N,N-dialkylamino wherein each alkyl group independently contains about 1 to about 6 carbon atoms; $R_9$ and $R_{10}$ are each independently hydrogen, hydroxy, lower alkyl having about 1 to about 6 carbon atoms, or lower alkoxy having about 1 to about 6 carbon atoms; $R_6$ and $R_7$ are each independently hydrogen or lower alkyl having about 1 to about 6 carbon atoms and each $R_6$ and $R_7$ is independently selected in each —O—$CHR_6$—$CHR_7$— unit; $R_8$ is hydrogen, alkyl having about 1 to about 100 carbon atoms, phenyl, aralkyl having about 7 to about 100 carbon atoms, or alkaryl having about 7 to about 100 carbon atoms; x is an integer from about 2 to about 5; y is an integer from about 0 to about 1; and z is an integer from about 5 to about 100.

The present invention further provides a fuel composition comprising a major amount of hydrocarbons boiling in the gasoline or diesel range and an effective deposit-controlling wherein A, $R_1$–$R_8$, x, y, and z are as defined above.

In formula I, above, A is preferably a hydroxy, nitro, or amino group. More preferably, A is a hydroxy or nitro group, and most preferably hydroxy.

Preferably, $R_1$ is hydrogen, hydroxy, or lower alkyl having about 1 to about 4 carbon atoms. More preferably, $R_1$ is hydrogen or hydroxy. Most preferably, $R_1$ is hydrogen. $R_2$, $R_3$, $R_5$, $R_6$, and $R_7$ are preferably hydrogen.

$R_4$ is hydrogen or an acyl group of the formula:

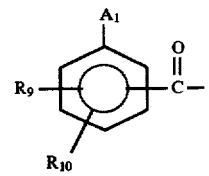

wherein $A_1$ is preferably a hydroxy, nitro, or amino group. More preferably, $A_1$ is a hydroxy or nitro group, and most preferably hydroxy. Preferably, $R_9$ is hydrogen, hydroxy, or lower alkyl having about 1 to about 4 carbon atoms. More preferably, $R_9$ is hydrogen. $R_{10}$ is preferably hydrogen.

Preferably, one of $R_6$ and $R_7$ is lower alkyl having about 1 to about 3 carbon atoms and the other hydrogen. More preferably, one of $R_6$ and $R_7$ is methyl or ethyl and the other is hydrogen. Most preferably, one of $R_6$ and $R_7$ is ethyl and the other is hydrogen.

Preferably, $R_8$ is hydrogen, alkyl having about 1 to about 30 carbon atoms, or alkylphenyl having an alkyl group containing about 1 to about 30 carbon atoms. More preferably, $R_8$ is hydrogen, alkyl having about 2 to about 24 carbon atoms, or alkylphenyl having an alkyl group containing about 2 to about 24 carbon atoms. Still more preferably, $R_8$ is hydrogen, alkyl having about 4 to about 12 carbon atoms or alkylphenyl having an alkyl group containing about 4 to about 12 carbon atoms. Most preferably, $R_8$ is alkylphenyl having an alkyl group containing about 4 to about 12 carbon atoms.

Preferably, x is an integer from about 2 to about 3. More preferably, x is 2. Preferably, y is 0. Preferably, z is an integer from about 8 to about 50, more preferably z is about 10 to about 30.

A preferred group of aromatic amides of the poly (oxyalkylene)carbamates are those of formula I wherein $R_1$ and $R_9$ are hydrogen, hydroxy, or lower alkyl having about 1 to about 4 carbon atoms; $R_2$, $R_3$, $R_5$, and $R_{10}$ are hydrogen; one of $R_6$ and $R_7$ is hydrogen and the other is methyl or ethyl; $R_8$ is hydrogen, alkyl having about 1 to about 30 carbon atoms, or alkylphenyl having an alkyl group containing about 1 to about 30 carbon atoms; x is 2; y is 1; and z is about 10 to about 30.

Another preferred group of aromatic amides of the poly (oxyalkylene)carbamates are those of formula I wherein $R_1$ and $R_9$ are hydrogen, hydroxy, or lower alkyl having about 1 to about 4 carbon atoms; $R_2$, $R_3$, $R_5$, and $R_{10}$ are hydrogen; one of R6 and $R_7$ is hydrogen and the other is methyl or ethyl; $R_8$ is hydrogen, alkyl having about 1 to about 30 carbon atoms, or alkylphenyl having an alkyl group containing about 1 to about 30 carbon atoms; x is 2; y is 0; and z is about 10 to about 30.

When A and $A_1$ are an N-alkylamino group, the alkyl group of the N-alkylamino moiety preferably contains about 1 to about 4 carbon atoms. More preferably, the alkyl group is methyl or ethyl. For example, particularly preferred N-alkylamino groups are N-methylamino and N-ethylamino groups. Most preferably, the alkyl group is methyl.

Similarly, when A and $A_1$ are an N,N-dialkylamino group, each alkyl group of the N,N-dialkylamino moiety preferably contains about 1 to about 4 carbon atoms. More preferably, each alkyl group is either methyl or ethyl. For example, particularly preferred N,N-dialkylamino groups are N,N-dimethylamino, N-ethyl-N-methylamino, and N,N-diethylamino groups. Most preferably, each alkyl group is methyl.

A further preferred group of aromatic amides of the poly(oxyalkylene)carbamates are those wherein A and $A_1$ are hydroxy; $R_1$ and $R_9$ are hydrogen or hydroxy; $R_2$, $R_3$, $R_5$, and $R_{10}$ are hydrogen; one of $R_6$ and $R_7$ is hydrogen and the other is methyl or ethyl; $R_8$ is hydrogen, alkyl having about 1 to about 30 carbon atoms, or alkylphenyl having an alkyl group containing about 1 to about 30 carbon atoms; x is 2; y is 1; and z is about 8 to about 50. A more preferred group of aromatic amides of the poly(oxyalkylene)carbamates are those wherein A and $A_1$ are hydroxy; $R_1$ and $R_9$ are hydrogen or hydroxy; $R_2$, $R_3$, $R_5$, and $R_{10}$ are hydrogen; one of $R_6$ and $R_7$ is hydrogen and the other is methyl or ethyl; $R_8$ is hydrogen, alkyl having about 2 to about 24 carbon atoms, or alkylphenyl having an alkyl group containing about 2 to about 24 carbon atoms; x is 2; y is 1; and z is about 10 to about 30. A particularly preferred group of aromatic amides of the poly(oxyalkylene)carbamates are those wherein A is hydroxy; $R_1$ and $R_9$ are hydrogen or hydroxy; $R_2$, $R_3$, $R_5$, and $R_{10}$ are hydrogen; one of $R_6$ and $R_7$ is hydrogen and the other is methyl or ethyl; $R_8$ is alkylphenyl having an alkyl group containing about 4 to about 12 carbon atoms; x is 2; y is 0; and z is about 10 to about 30.

It is especially preferred that the hydroxy, nitro, amino, N-alkylamino, or N,N-dialkylamino substituent present in the aromatic moiety of aromatic amides of this invention be situated in a meta or para position relative to the amide moiety of the poly(oxyalkylene)carbamate. When $R_1$ or $R_9$ is a hydroxy or lower alkyl having about 1 to about 4 carbon atoms, it is particularly preferred that the hydroxy or lower alkyl groups be in a meta or para position relative to the amide moiety of the poly(oxyalkylene)carbamate and in an ortho position relative to the hydroxy, nitro, amino, N-alkylamino, or N,N-dialkylamino substituent.

The aromatic amides of poly(oxyalkylene)carbamates of the present invention will generally have a sufficient molecular weight so as to be non-volatile at normal engine intake valve operating temperatures (about 200° C. to about 250° C.). Typically, the molecular weight of the poly (oxyalkylene)carbamates of this invention will range from about 450 to about 5,000, preferably from about 500 to about 3,000, more preferably from about 600 to about 2,000.

Fuel-soluble salts of the hydroxy aromatic amides of poly(oxyalkylene)carbamates of the present invention are also contemplated to be useful for preventing or controlling deposits. Such salts include alkali metal, alkaline earth metal, ammonium, substituted ammonium, and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Fuel-soluble salts of the amino aromatic amides of poly (oxyalkylene)carbamates of the present invention can be readily prepared from those compounds containing an amino, N-alkylamino, or N,N-dialkylamino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

DEFINITIONS

As used herein, the following terms have the following meanings unless expressly stated to the contrary.

The term "amino" refers to the group:—$NH_2$.

The term "hydroxy" refers the group:—OH.

The term "nitro" refers to the group:—$NO_2$.

The term "N-alkylamino" refers to the group:—$NHR_a$ wherein $R_a$ is an alkyl group.

The term "N,N-dialkylamino" refers to the group:— $NR_bR_c$, wherein $R_b$ and $R_c$ are alkyl groups.

The term "alkyl" refers to both straight- and branched-chain alkyl groups.

The term "lower alkyl" refers to alkyl groups having about 1 to about 6 carbon atoms and includes primary, secondary, and tertiary alkyl groups. Typical lower alkyl groups include, for example, methyl, ethyl, n-propyl, isopropyl, n-butyl, sec-butyl, t-butyl, n-pentyl, n-hexyl, and the like.

The term "alkaryl" refers to the group:

wherein $R_d$ and $R_e$ are each independently hydrogen or an alkyl group, with the proviso that both $R_d$ and $R_e$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl, and the like.

The term "alkylphenyl" refers to an alkaryl group of the above formula in which $R_d$ is alkyl and $R_e$ is hydrogen.

The term "aralkyl" refers to the group:

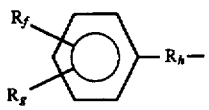

wherein $R_f$ and $R_g$ are each independently hydrogen or an alkyl group; and $R_h$ is an alkylene group. Typical alkaryl groups include, for example, benzyl, methylbenzyl, dimethylbenzyl, phenethyl, and the like.

The term "hydrocarbyl" refers to an organic radical primarily composed of carbon and hydrogen which may be aliphatic, aromatic or combinations thereof (e.g., aralkyl or alkaryl). Such hydrocarbyl groups are generally relatively free of aliphatic unsaturation, i.e., olefinic or acetylenic unsaturation, but may contain minor amounts of heteroatoms, such as oxygen or nitrogen, or halogens, such as chlorine.

The term "oxyalkylene unit" refers to an ether moiety having the general formula:

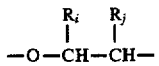

wherein $R_i$ and $R_j$ are each independently hydrogen or lower alkyl groups.

The term "poly(oxyalkylene)" refers to a polymer or oligomer having the general formula:

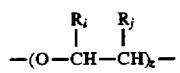

wherein $R_i$ and $R_j$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

GENERAL SYNTHETIC PROCEDURES

The hydroxy, nitro, and amino aromatic amides of the poly(oxyalkylene)carbamates of the present invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Moreover, those skilled in the art will recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

In the present synthetic procedures, a hydroxy group will preferably be protected, when necessary, as the benzyl or tert-butyldimethylsilyl ether. Introduction and removal of these protecting groups are well described in the art. Amino groups may also require protection and this may be accomplished by employing a standard amino protecting group, such as a benzyloxycarbonyl or a trifluoroacetyl group. Additionally, as will be discussed in further detail below, the aromatic amides of the poly(oxyalkylene)carbamates of this invention having an amino group on the aromatic moiety will generally be prepared from the corresponding nitro derivative. Accordingly, in many of the following procedures, a nitro group will serve as a protecting group for the amino moiety.

The aromatic amides of poly(oxyalkylene)carbamates of the present invention having the formula:

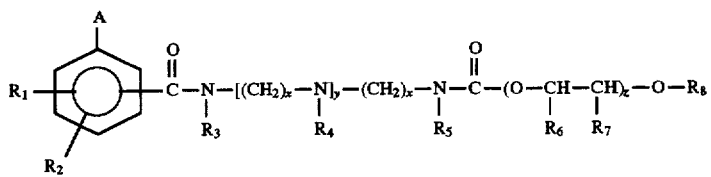

(I)

wherein A, $R_1$–$R_8$, x, y, and z are as defined above may be prepared by conventional reaction conditions by reacting an acyl halide having the formula:

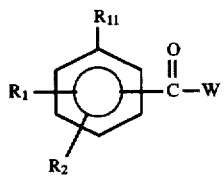

(II)

wherein $R_1$ and $R_2$ are as defined above, $R_{11}$ is a nitro or protected hydroxy or amino group, and W is a halide, such as chloride or bromide, with a poly(oxyalkylene)carbamate substituted amine having the formula:

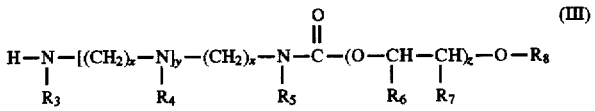

(III)

wherein $R_3$–$R_8$, x, y, and z are as defined above.

A. Preparation of the Acyl Halide

Acyl halides of formula II may be prepared from the corresponding aromatic carboxylic acids by first protecting the hydroxy or amino groups as necessary to form a carboxylic acid having the formula:

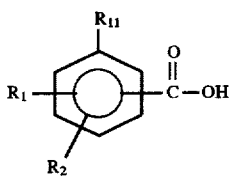

(IV)

wherein $R_1$ and $R_2$ are as defined above and $R_{11}$ is nitro or a suitably protected hydroxy or amino group.

The aromatic carboxylic acids which are first protected and then converted to the corresponding acyl halide are either known compounds or can be prepared from known compounds by conventional procedures. Representative aromatic carboxylic acids suitable for use as starting materials include, for example, 2-hydroxybenzoic acid, 3-hydroxybenzoic acid, 4-hydroxybenzoic acid, 3,4-dihydroxybenzoic acid, 3,4,5-trihydroxybenzoic acid, 3-hydroxy-4-methoxybenzoic acid, 4-hydroxy-3-methoxybenzoic acid, 3-t-butyl-4-hydroxybenzoic acid, 3,5-di-t-butyl-4-hydroxybenzoic acid, 2-nitrobenzoic acid, 3-nitrobenzoic acid, 4-nitrobenzoic acid, 3-hydroxy-4-nitrobenzoic acid, 4-hydroxy-3-nitrobenzoic acid, 2-aminobenzoic acid (anthranilic acid), 3-aminobenzoic acid, 4-aminobenzoic acid, 3-amino-4-hydroxybenzoic acid, 4-amino-3-hydroxybenzoic acid, 3-amino-4-methoxybenzoic acid, 4-amino-3-methoxybenzoic acid, 4-amino-3-methylbenzoic acid, 4-amino-3,5-di-t-butylbenzoic acid, 3-(N-methylamino)benzoic acid, 4-(N-methylamino)benzoic acid, 3-(N-ethylamino)benzoic acid, 4-(N-ethylamino)benzoic acid, 3-(N,N-dimethylamino) benzoic acid, 4-(N,N-dimethylamino)benzoic acid, and the like.

Preferred aromatic carboxylic acids include 3-hydroxybenzoic acid, 4-amino-3-hydroxybenzoic acid, 3-nitrobenzoic acid, 4-nitrobenzoic acid, 3-hydroxy-4-nitrobenzoic acid, 4-hydroxy-3-nitrobenzoic acid, 3-aminobenzoic acid, 4-aminobenzoic acid, 3-amino-4-hydroxybenzoic acid, and 4-amino-3-hydroxybenzoic acid.

When the aromatic carboxylic acid contains a hydroxy group, for example, when A or $R_1$ is hydroxy, protection of the aromatic hydroxy groups may be accomplished using well-known procedures. The choice of a suitable protecting group for a particular hydroxy aromatic carboxylic acid will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein.

Deprotection of the aromatic hydroxy group(s) can also be accomplished using conventional procedures. Appropriate conditions for this deprotection step will depend upon the protecting group(s) utilized in the synthesis and will be readily apparent to those skilled in the art. For example, benzyl protecting groups may be removed by hydrogenolysis under about 1 to about 4 atmospheres of hydrogen in the presence of a catalyst, such as palladium on carbon. Typically, this deprotection reaction is conducted in an inert solvent, preferably a mixture of ethyl acetate and acetic acid, at a temperature of from about 0°C. to about 40° C. for about 1 to about 24 hours.

When synthesizing the aromatic amides of the poly (oxyalkylene)carbamates of formula I having an amino group on the aromatic moiety (i.e., where A is an amino group), it is generally desirable to first prepare the corresponding nitro compound (i.e., where A is a nitro group) and then to reduce the nitro group to an amino group using conventional procedures. Aromatic nitro groups may be reduced to amino groups using a number of procedures that are well known in the art. For example, aromatic nitro groups may be reduced under catalytic hydrogenation conditions; or by using a reducing metal, such as zinc, tin, iron, and the like, in the presence of an acid, such as dilute hydrochloric acid.

Generally, reduction of the nitro group by catalytic hydrogenation is preferred. Typically, this reaction is conducted using about 1 to about 4 atmospheres of hydrogen and a platinum or palladium catalyst, such as palladium on carbon. The reaction is typically carried out at a temperature of about 0° C. to about 100° C. for about 1 to about 24 hours in an inert solvent, such as ethanol, ethyl acetate, toluene, and the like. Hydrogenation of aromatic nitro groups is discussed in further detail in, for example, P. N. Rylander, *Catalytic Hydrogenation in Organic Synthesis*, pp. 113–137, Academic Press (1979); and *Organic Synthesis, Collective Vol. I*, Second Edition, pp. 240–241, John Wiley & Sons, Inc. (1941); and references cited therein.

In certain cases where the hydroxy aromatic carboxylic acids have bulky alkyl groups adjacent to the hydroxy group, such as 3,5-di-t-butyl-4-hydroxybenzoic acid, it will generally not be necessary to protect the hydroxy group prior to formation of the acyl halide, since such hydroxy groups are sufficiently sterically hindered so as to be substantially non-reactive with the halide moiety.

The acyl halide of formula II may then be prepared by reacting the protected aromatic carboxylic acid with an inorganic halide, such as thionyl chloride, phosphorous trichloride, phosphorous tribromide, or phosphorous pentachloride; or with oxalyl chloride, using conventional procedures.

Typically, this reaction will be conducted using about 1 to about 5 molar equivalents of the inorganic acyl halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

B. Preparation of the Poly(oxyalkylene)Carbamate Substituted Amine

The poly(oxyalkylene)carbamate substituted amine of formula III may be formed as the reaction product of a nitrogen-containing compound selected from a polyamine having from about 2 to about 3 nitrogen atoms and from about 2 to about 10 carbon atoms and a poly(oxyalkylene) chloroformate. The poly(oxyalkylene) chloroformate is prepared from a poly(oxyalkylene) alcohol having the formula:

(V)

wherein R6, $R_7$, and z are as defined above, and $R_8$ is alkyl, phenyl, aralkyl or alkaryl, by reaction with phosgene or a phosgene equivalent.

Alternatively the terminal hydroxy group on the poly (oxyalkylene) alcohol of formula V may first be converted to a suitable leaving group, such as a mesylate, chloride, bromide, and the like, prior to reaction with the nitrogen-containing compound.

The poly(oxyalkylene) alcohols of formula V are known compounds that can be prepared using conventional procedures. For example, suitable procedures for preparing such compounds are taught in U.S. Pat. Nos. 2,782,240 and 2,841,479, the disclosures of which are incorporated herein by reference.

Preferably, the poly(oxyalkylene) alcohols of formula V are prepared by contacting an alkoxide or phenoxide metal salt having the formula:

$$R_{12}-O-M \quad (VI)$$

wherein $R_{12}$ is an alkyl, phenyl, aralkyl, or alkaryl group and M is a metal cation, such as lithium, sodium, potassium, and the like, with about 5 to about 100 molar equivalents of an alkylene oxide (an epoxide) having the formula:

wherein $R_6$ and $R_7$ are as defined above.

Typically, metal salt VI is prepared by contacting the corresponding hydroxy compound $R_{12}OH$ with a strong base, such as sodium hydride, potassium hydride, sodium amide, and the like, in an inert solvent, such as toluene, xylene, and the like, under substantially anhydrous conditions at a temperature in the range from about $-10°$ C. to about $120°$ C. for about 0.25 to about 3 hours.

Metal salt VI is generally not isolated, but is reacted in situ with alkylene oxide VII to provide, after neutralization, the poly(oxyalkylene) alcohol V. This polymerization reaction is typically conducted in a substantially anhydrous inert solvent at a temperature of about $30°$ C. to about $150°$ C. for about 2 to about 120 hours. Suitable solvents for this reaction, include toluene, xylene, and the like. Typically, the reaction is conducted at a pressure sufficient to contain the reactants and the solvent, preferably at atmospheric or ambient pressure.

The amount of alkylene oxide employed in this reaction will generally depend on the number of oxyalkylene units desired in the product. Typically, the molar ratio of alkylene oxide VII to metal salt VI will range from about 5:1 to about 100:1; preferably, from about 8:1 to about 50:1, more preferably from about 10:1 to about 30:1.

Alkylene oxides suitable for use in this polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides; and the like. Preferred alkylene oxides are propylene oxide and 1,2-butylene oxide.

In the polymerization reaction, a single type of alkylene oxide may be employed, e.g., propylene oxide, in which case the product is a homopolymer, e.g., a poly(oxypropylene) polymer. Copolymers are equally satisfactory and random copolymers can be prepared by contacting metal salt VI with a mixture of alkylene oxides, such as a mixture of propylene oxide and 1,2-butylene oxide, under polymerization conditions. Copolymers containing blocks of oxyalkylene units are also suitable for use in this invention. Block copolymers can be prepared by contacting metal salt VI with first one alkylene oxide, then others in any order, or repetitively, under polymerization conditions.

Poly(oxyalkylene) copolymers prepared by terminating or capping the poly(oxyalkylene) moiety with about 1 to about 10 oxyethylene units, preferably about 2 to about 5 oxyethylene units, are particularly useful in the present invention, since these copolymers have been found to be more readily esterified than those having an alkyl branch in the terminal oxyalkylene unit. These copolymers may be prepared by contacting metal salt VI with an alkylene oxide of formula VII, such as propylene oxide or 1,2-butylene oxide, under polymerization conditions and then capping or terminating the resulting block of oxyalkylene units with oxyethylene units by adding ethylene oxide.

The poly(oxyalkylene) alcohol V may also be prepared by living or immortal polymerization as described by S. Inoue and T. Aida in *Encyclopedia of Polymer Science and Engineering*, Second Edition, Supplemental Volume, J. Wiley and Sons, New York, pp. 412–420 (1989). These procedures are especially useful for preparing poly (oxyalkylene) alcohols of formula V in which $R_6$ and $R_7$ are both alkyl groups.

As noted above, the alkoxide or phenoxide metal salt used in the above procedures is generally derived from the corresponding hydroxy compound, $R_{12}OH$. Suitable hydroxy compounds include straight- or branched-chain aliphatic alcohols having about 1 to about 100 carbon atoms and phenols having the formula:

wherein $R_{13}$ is an alkyl group having about 1 to about 100 carbon atoms and $R_{14}$ is hydrogen; or $R_{13}$ and $R_{14}$ are both alkyl groups, each independently containing about 1 to about 50 carbon atoms.

Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having about 9 to about 100 carbon atoms and polybutene alcohols having about 12 to about 100 carbon atoms. Preferred straight- or branched-chain aliphatic alcohols will contain about 1 to about 30 carbon atoms, more preferably about 2 to about 24 carbon atoms, and most preferably about 4 to about 12 carbon atoms. Particularly preferred aliphatic alcohols are butanols.

The phenols of formula VIII may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenol will contain about 1 to about 30 carbon atoms, more preferably about 2 to about 24 carbon atoms, and most preferably about 4 to about 12 carbon atoms. Representative examples of phenols suitable for use in this invention include, but are not limited to, phenol, methylphenol, dimethylphenol, ethylphenol, butylphenol, octylphenol, decylphenol, dodecylphenol, tetradecylphenol, hexadecylphenol, octaphenol, eicosylphenol, tetracosylphenol, hexacosylphenol, triacontylphenol, and the like. Also, mixtures of alkylphenols may be employed, such as a mixture of $C_{14}$ to $C_{18}$ alkylphenols, a mixture of $C_{18}$ to $C_{24}$ alkylphenols, a mixture of $C_{20}$ to $C_{24}$ alkylphenols, or a mixture of $C_{16}$ to $C_{26}$ alkylphenols.

Particularly preferred alkylphenols are prepared by alkylating phenol with polymers or oligomers of $C_3$ to $C_6$ olefins, such as polypropylene or polybutene. These polymers typically contain about 8 to about 100 carbon atoms, preferably about 10 to about 30 carbon atoms. An especially preferred alkylphenol is prepared by alkylating phenol with a propylene polymer having an average of 4 units. This polymer has the common name of propylene tetramer and is commercially available.

The amine component of the poly(oxyalkylene)carbamate substituted amine may be derived from a primary monoamine or a polyamine having terminal amino nitrogen atoms. Primary monoamines useful in preparing compounds of the present invention contain 1 nitrogen atom and from about 1 to about 6 carbon atoms. Examples of suitable monoamines include N-methylamine, N-ethylamine, N-n-propylamine, N-isopropylamine, N-n-butylamine, N-isobutylamine, N-sec-butylamine, N-tert-butylamine, N-n-pentylamine, and N-n-hexylamine. Preferred primary amines are N-methylamine, N-ethylamine, and N-n-propylamine.

When the amine component is derived from a polyamine, the polyamine will be either an alkylene diamine or a dialkylene triamine. The alkylene group will contain from about 2 to about 5 carbon atoms, preferably from about 2 to about 3 carbon atoms. Examples of such polyamines include ethylene diamine, propylene diamine, isopropylene diamine, butylene diamine, isobutylene diamine, pentylene diamine, diethylene triamine, dipropylene triamine, diisopropylene triamine, dibutylene triamine, diisobutylene triamine, and dipentylene triamine. Preferred polyamines are ethylene diamine and diethylene triamine.

The carbamate connecting group which covalently links the poly(oxyalkylene) component to the amine component has the formula:

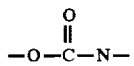

wherein the ether oxygen may be regarded as being derived from the hydroxyl group of a poly(oxyalkylene) alcohol of formula V; and the nitrogen atom may be regarded as being derived from a nitrogen atom of a suitable amine component. The carbonyl group, —C(O)—, is preferably provided by a carbonyl-containing coupling agent, such as phosgene or a phosgene equivalent. Economically, phosgene is the preferred coupling agent. Alternatively, suitable phosgene equivalents include, for example, 1,1'-carbonyldiimidazole, trichloromethyl chloroformate (diphosgene), and bis(trichloromethyl)carbonate (triphosgene).

The poly(oxyalkylene)carbamate substituted amines are preferably prepared by contacting a poly(oxyalkylene) alcohol of formula V with phosgene to produce a poly(oxyalkylene) chloroformate. The chloroformate is then contacted with a suitable polyamine to afford a poly(oxyalkylene)carbamate substituted amine.

The reaction of the poly(oxyalkylene) alcohol of formula V with phosgene is typically conducted on an essentially equimolar basis, although excess phosgene can be used to increase the yield of the chloroformate. Excess phosgene is typically removed from the reaction mixture by stripping at reduced pressure before addition of the polyamine. The reaction may be conducted by contacting the poly(oxyalkylene) alcohol with phosgene at temperatures ranging from about −10° C. to about 200° C., typically in an inert solvent, such as benzene, toluene, and the like, for about 0.25 to about 5 hours.

A poly(oxyalkylene)carbamate substituted amine is then formed by contacting the poly(oxyalkylene) chloroformate with a suitable polyamine at a temperature ranging from about 0° C. to about 150° C. for about 1 to about 24 hours. This reaction may be conducted with or without an inert solvent. Suitable inert solvents include benzene, toluene, and the like. The molar ratio of polyamine to poly(oxyalkylene) chloroformate will generally range from about 2:1 to about 20:1, preferably about 5:1 to about 10:1. The desired product may be obtained by washing the reaction mixture with water and stripping the mixture, usually under vacuum, to remove any residual solvent.

The poly(oxyalkylene) carbamate substituted amines employed to make the aromatic amides of this invention are prepared by conventional procedures known in the art. Such poly(oxyalkylene)carbamate substituted amines and their preparations are further described in detail in U.S. Pat. Nos. 4,236,020 and 4,288,612 both to Lewis et al. and 4,881,945 to Buckley, the disclosures of which are incorporated herein by reference for all purposes.

C. Preparation of the Aromatic Amide of the Poly(oxyalkylene)Carbamate

Reaction of the acyl halide of formula II with a poly(oxyalkylene)carbamate substituted amine of formula III provides an aromatic amide of the poly(oxyalkylene) carbamate shown as formula I.

Typically, this reaction is conducted by contacting a poly(oxyalkylene)carbamate substituted amine with about 1 to about 3.5 molar equivalents of an acyl halide of formula II in an inert solvent, such as toluene, dichloromethane, diethyl ether, and the like, at a temperature in the range of about 25° C. to about 150° C. The reaction is generally complete in about 0.5 to about 48 hours. Preferably, the reaction is conducted in the presence of a sufficient amount of an amine capable of neutralizing the acid generated during the reaction, such as triethylamine, di(isopropyl)ethylamine, pyridine, or 4-dimethylamino-pyridine.

The aromatic amides of poly(oxyalkylene)carbamates of formula I wherein $R_8$ is hydrogen, i.e., compounds having the formula:

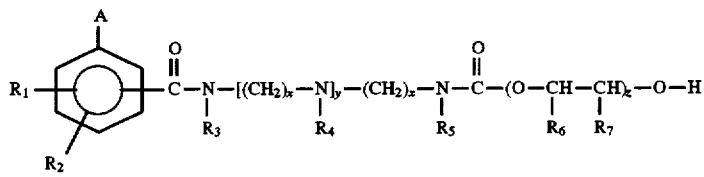

(IX)

wherein A, $R_1$–$R_7$, x, y, and z are as defined above, may be prepared from compounds of formula I wherein $R_8$ is a labile hydrocarbyl group, such as benzyl or t-butyl group, by removing the hydrocarbyl group under appropriate conditions to provide a hydroxyl group. For example, compounds where $R_8$ represents a benzyl group may be prepared by employing a metal salt VI derived from benzyl alcohol in the above-described synthetic procedures. Cleavage of the benzyl ether using conventional hydrogenolysis procedures then provides a compound of formula IX. Other labile hydrocarbyl groups, such as a t-butyl group, may be similarly employed for those compounds having functional groups that are not compatible with hydrogenolysis conditions, such as nitro groups. t-Butyl ethers may be cleaved under acidic conditions using, for example, trifluoroacetic acid.

FUEL COMPOSITIONS

The aromatic amide poly(oxyalkylene)carbamates of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the aromatic amide poly (oxyalkylene)carbamates of this invention in hydrocarbon fuel will range from about 50 to about 2,500 parts per million (ppm) by weight, preferably from about 75 to about 1,000 ppm. When other deposit control additives are present, a lesser amount of the present additive may be used.

The aromatic amide poly(oxyalkylene)carbamates of the present invention may be formulated as a concentrate using an inert stable oxophilic (i.e., dissolved in gasoline) organic solvent boiling in the range of about 150° F. to about 400° F. (about 65° C. to about 205° C.). Preferably, an aliphatic or an aromatic hydrocarbon solvent is used, such as benzene, toluene, xylene, or higher-boiling aromatics or aromatic thinners. Aliphatic alcohols containing about 3 to about 8 carbon atoms, such as isopropanol, isobutylcarbinol, n-butanol, and the like, in combination with hydrocarbon solvents are also suitable for use with the present additives. In the concentrate, the amount of the additive will generally range from about 10 to about 70 weight percent, preferably about 10 to about 50 weight percent, more preferably from about 20 to about 40 weight percent.

In gasoline fuels, other fuel additives may be employed with the additives of the present invention, including, for example, oxygenates, such as t-butyl methyl ether, anti-knock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators, and demulsifiers may be present.

In diesel fuels, other well-known additives can be employed, such as pour point depressants, flow improvers, cetane improvers, and the like.

A fuel-soluble, nonvolatile carrier fluid or oil may also be used with the aromatic amide poly(oxyalkylene)carbamates of this invention. The carrier fluid is a chemically inert hydrocarbon-soluble liquid vehicle which substantially increases the nonvolatile residue (NVR) or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis and U.S. Pat. No. 4,877,416 to Campbell, and polyesters, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with an aromatic amide poly(oxyalkylene) carbamate of this invention.

The carrier fluids are typically employed in amounts ranging from about 100 to about 5,000 ppm by weight of the hydrocarbon fuel, preferably from about 400 to about 3,000 ppm of the fuel. Preferably, the ratio of carrier fluid to deposit control additive will range from about 0.5:1 to about 10:1, more preferably from about 1:1 to about 4:1, most preferably about 2:1.

When employed in a fuel concentrate, carrier fluids will generally be present in amounts ranging from about 20 to about 60 weight percent, preferably from about 30 to about 50 weight percent.

EXAMPLES

The following examples are presented to illustrate specific embodiments of the present invention and synthetic preparations thereof; and should not be interpreted as limitations upon the scope of the invention.

Example 1

Preparation of 4-Benzyloxybenzoyl chloride

To a flask equipped with a magnetic stirrer and drying tube was added 4-benzyloxybenzoic acid (30.0 grams), anhydrous dichloromethane (200 mL), and then oxalyl chloride (28.7 mL). The resulting mixture was stirred at room temperature for 16 hours and the solvent removed in vacuo to yield 43.2 grams of the desired acid chloride as a white solid.

Example 2

Preparation of

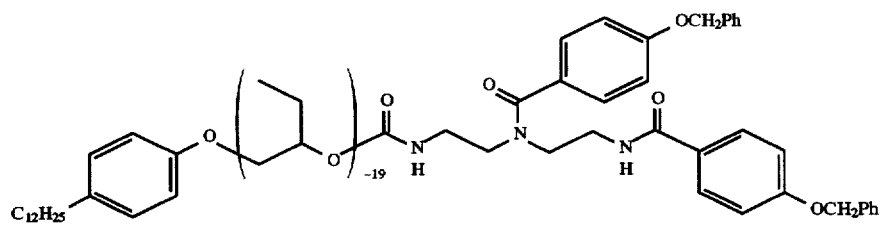

Dodecylphenyl poly(oxybutylene) diethylenetriamine carbamate having an average of 19 oxybutylene units (prepared essentially as described in Examples 6–8 of U.S. Pat. No. 4,160,648) was chromatographed on silica gel eluting with hexane/diethyl ether (1:1) followed by hexane/ diethyl ether/methanol/isopropylamine (40:40:15:5). 4-Benzyloxybenzoyl chloride (6.8 grams, prepared as in Example 1) was combined with 25.0 grams of chromatographed dodecylphenyl poly(oxybutylene) diethylenetriamine carbamate and anhydrous toluene (250 mL). Triethylamine (4.0 mL) and 4-dimethylamino pyridine (1.7 grams) were then added and the resulting mixture was heated to reflux under nitrogen for 16 hours. The reaction was diluted with 750 mL of hexane and was washed twice with 1% aqueous hydrochloric acid, twice with saturated aqueous sodium bicarbonate solution and once with brine. The organic layer was dried over anhydrous magnesium sulfate, filtered and the solvents removed in vacuo to yield 26.6 grams of a yellow-brown oil. The oil was chromatographed on silica gel, eluting with diethyl ether/isopropylamine (95:5) to afford 10.3 grams of the desired product as a yellow oil.

Example 3
Preparation of

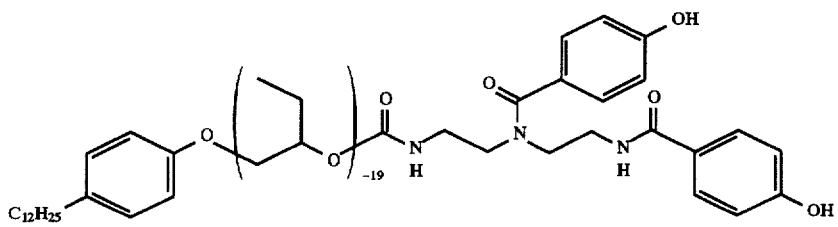

A solution of 20.8 grams of the product from Example 2 in 100 mL of ethyl acetate and 100 mL of acetic acid containing 3.0 grams of 10% palladium on charcoal was hydrogenolyzed at 35–40 psi for 16 hours on a Parr low-pressure hydrogenator. Catalyst filtration and removal of the residual acetic acid with toluene in vacuo yielded 9.8 grams of the desired product as a yellow-brown oil. IR (neat) 1709 cm$^{-1}$, 1636 cm$^{-1}$; $^1$H NMR (CDCl$_3$, D$_2$O) δ6.4–7.7 (m, 12H), 4.5–4.7 (m,1H), 3.1–4.2 (m, 64H), 0.6–1.8 (m, 120H).

Example 4
Preparation of

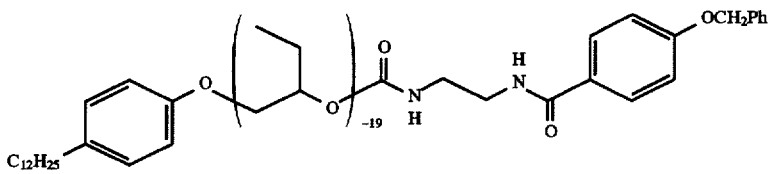

Dodecylphenyl poly(oxybutylene) ethylenediamine carbamate having an average of 19 oxybutylene units (prepared essentially as described in Examples 6–8 of U.S. Pat. No. 4,160,648) was chromatographed on silica gel eluting with hexane/diethyl ether (1:1) followed by hexane/diethyl ether/methanol/isopropylamine (40:40:15:5). 4-Benzyloxybenzoyl chloride (3.0 grams, prepared as in Example 1) was combined with 21.5 grams of chromatographed dodecylphenyl poly(oxybutylene) ethylenediamine carbamate and anhydrous dichloromethane (300 mL). Triethylamine (1.9 mL) was then added and the resulting mixture was stirred at room temperature under nitrogen for 16 hours. The reaction was diluted with 750 mL of dichloromethane and was washed twice with 1% aqueous hydrochloric acid, twice with saturated aqueous sodium bicarbonate solution and once with brine. The organic layer was dried over anhydrous magnesium sulfate, filtered and the solvents removed in vacuo to yield 24.0 grams of a yellow oil. The oil was chromatographed on silica gel, eluting with hexane/ethyl acetate/ethanol (90:8:2) to afford 11.2 grams of the desired product as a yellow oil.

Example 5
Preparation of

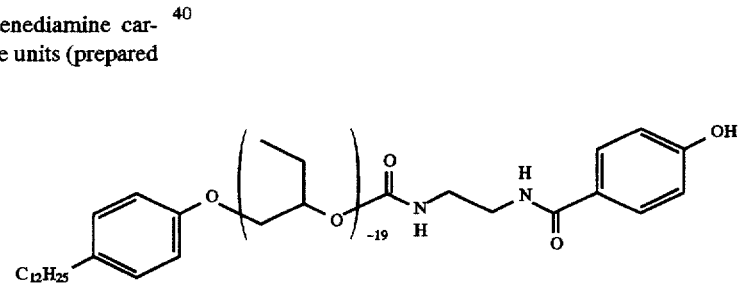

A solution of 11.2 grams of the product from Example 4 in 100 mL of ethyl acetate and 100 mL of acetic acid containing 2.5 grams of 10% palladium on charcoal was hydrogenolyzed at 35–40 psi for 16 hours on a Parr low-pressure hydrogenator. Catalyst filtration and removal of the residual acetic acid with toluene in vacuo yielded 10.4 grams of the desired product as a yellow oil. IR (neat) 1715 cm$^{-1}$, 1639 cm$^{-1}$; $^1$H NMR (CDCl$_3$, D$_2$O) δ6.4–7.7 (m, 8H), 4.5–4.7 (m,1H), 3.1–4.2 (m, 60H), 0.6–1.8 (m, 120H).

Example 6
Single-Cylinder Engine Test

The test compounds were blended in gasoline and their deposit reducing capacity determined in an ASTM/CFR single-cylinder engine test. A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40 ° BTC; engine speed is 1800 rpm; the crankcase oil is a commercial 30 W oil.

The amount of carbonaceous deposit in milligrams on the intake valves is reported for each of the test compounds in Table I.

TABLE I

Single-Cylinder Engine Test Results

| Sample[1] | Intake Valve Deposit Weight (in milligrams) | | |
|---|---|---|---|
| | Run 1 | Run 2 | Average |
| Base Fuel | 164.4 | 158.1 | 161.3 |
| Example 3 | 3.4 | 4.0 | 3.7 |
| Example 5 | 10.0 | 5.5 | 7.8 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by an aromatic amide poly (oxyalkylene) carbamate of the present invention (Examples 3 and 5) compared to the base fuel.

What is claimed is:

1. A compound of the formula:

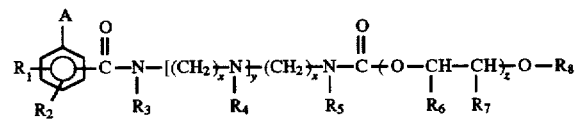

or a fuel-soluble salt thereof;

wherein A is hydroxy, nitro, amino, N-alkylamino wherein the alkyl group contains about 1 to about 6 carbon atoms, or N,N-dialkylamino wherein each alkyl group independently contains about 1 to about 6 carbon atoms;

$R_1$ and $R_2$ are each independently hydrogen, hydroxy, lower alkyl having about 1 to about 6 carbon atoms, or lower alkoxy having about 1 to about 6 carbon atoms;

$R_3$ and $R_5$ are each independently hydrogen or lower alkyl having about 1 to about 6 carbon atoms;

$R_4$ is hydrogen or an acyl group of the formula:

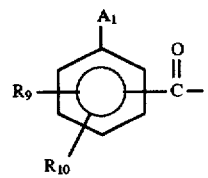

wherein $A_1$ is hydroxy, nitro, amino, N-alkylamino wherein the alkyl group contains about 1 to about 6 carbon atoms, or N,N-dialkylamino wherein each alkyl group independently contains about 1 to about 6 carbon atoms;

$R_9$ and $R_{10}$ are each independently hydrogen, hydroxy, lower alkyl having about 1 to about 6 carbon atoms, or lower alkoxy having about 1 to about 6 carbon atoms;

$R_6$ and $R_7$ are each independently hydrogen or lower alkyl having about 1 to about 6 carbon atoms and each $R_6$ and $R_7$ is independently selected in each —O—$CHR_6$—$CHR_7$— unit;

$R_8$ is hydrogen, alkyl having about 1 to about 100 carbon atoms, phenyl, aralkyl having about 7 to about 100 carbon atoms, or alkaryl having about 7 to about 100 carbon atoms;

x is an integer from about 2 to about 5; y is an integer from about 0 to about 1; and z is an integer from about 5 to about 100.

2. The compound according to claim 1, wherein A and $A_1$ are each independently hydroxy, nitro, or amino.

3. The compound according to claim 1, wherein A and $A_1$ are each hydroxy.

4. The compound according to claim 1, wherein A and $A_1$ are each nitro.

5. The compound according to claim 1, wherein $R_1$ and $R_9$ are each independently hydrogen, hydroxy, or lower alkyl having about 1 to about 6 carbon atoms.

6. The compound according to claim 5, wherein $R_1$ and $R_9$ are each independently hydrogen or hydroxy.

7. The compound according to claim 6, wherein $R_1$ and $R_9$ are hydrogen.

8. The compound according to claim 7, wherein A and $A_1$ are each hydroxy.

9. The compound according to claim 1, wherein $R_2$ and $R_{10}$ are hydrogen.

10. The compound according to claim 9, wherein $R_3$ and $R_5$ are hydrogen.

11. The compound according to claim 1, wherein one of $R_6$ and $R_7$ is lower alkyl having about 1 to about 3 carbon atoms and the other is hydrogen.

12. The compound according to claim 11, wherein one of $R_6$ and $R_7$ is methyl or ethyl and the other is hydrogen.

13. The compound according to claim 1, wherein $R_8$ is hydrogen, alkyl having about 1 to about 30 carbon atoms, or alkylphenyl having an alkyl group containing about 1 to about 30 carbon atoms.

14. The compound according to claim 13, wherein $R_8$ is hydrogen, alkyl having about 2 to about 24 carbon atoms, or alkylphenyl having an alkyl group containing about 2 to about 24 carbon atoms.

15. The compound according to claim 14, wherein $R_8$ is alkylphenyl having an alkyl group containing about 4 to about 12 carbon atoms.

16. The compound according to claim 15, wherein said alkyl group is derived from propylene tetramer.

17. The compound according to claim 1, wherein x is 2 and y is 1.

18. The compound according to claim 17, wherein x is 2 and y is 0.

19. The compound according to claim 1, wherein z is about 8 to about 50.

20. The compound according to claim 19, wherein z is about 10 to about 30.

* * * * *